United States Patent [19]
Campbell et al.

[11] Patent Number: 4,547,502
[45] Date of Patent: Oct. 15, 1985

[54] DIHYDROPYRIDINES AND THEIR USE IN TREATING CARDIAC CONDITIONS AND HYPERTENSION

[75] Inventors: Simon F. Campbell, Deal; Peter E. Cross, Canterbury; John K. Stubbs, Deal, all of England

[73] Assignee: Pfizer Inc., New York, N.Y.

[21] Appl. No.: 528,508

[22] Filed: Sep. 1, 1983

Related U.S. Application Data

[63] Continuation-in-part of Ser. No. 463,096, Feb. 2, 1983, abandoned.

[30] Foreign Application Priority Data

Sep. 4, 1982 [GB] United Kingdom ............... 8225245

[51] Int. Cl.[4] ................ A61K 31/495; C07D 401/14; C07D 417/14
[52] U.S. Cl. ............................ 514/253; 514/252; 544/295; 544/364; 544/365; 544/399
[58] Field of Search ............... 544/364, 295; 424/250, 424/251

[56] References Cited

U.S. PATENT DOCUMENTS

| | | | |
|---|---|---|---|
| 3,362,956 | 1/1968 | Archer | 544/364 |
| 3,787,411 | 1/1974 | Ruschig et al. | 544/364 |
| 3,905,983 | 9/1975 | Bossert et al. | |
| 3,943,140 | 3/1976 | Bossert et al. | |
| 3,946,027 | 3/1976 | Bossert et al. | 424/258 |
| 3,946,028 | 3/1976 | Bossert et al. | |
| 4,177,278 | 12/1979 | Bossert et al. | 424/266 |
| 4,188,395 | 2/1980 | Bossert et al. | 424/266 |

FOREIGN PATENT DOCUMENTS

| | | |
|---|---|---|
| 0031801 | 7/1981 | European Pat. Off. |
| 0060674 | 9/1982 | European Pat. Off. |
| 55-47656 | 4/1980 | Japan |
| 1552911 | 9/1979 | United Kingdom |
| 2034693 | 6/1980 | United Kingdom |
| 1585978 | 3/1981 | United Kingdom |

Primary Examiner—Glennon H. Hollrah
Assistant Examiner—James H. Turnipseed

Attorney, Agent, or Firm—Charles J. Knuth; Albert E. Frost; James M. McManus

[57] ABSTRACT

1,4-Dihydropyridine derivatives of the formula

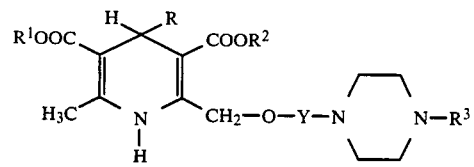

and their pharmaceutically acceptable acid addition salts;

where:

R is aryl or heteroaryl;
$R^1$ and $R^2$ are each independently $C_1$-$C_4$ alkyl or 2-methoxyethyl;
Y is $-(CH_2)_2-$, $-(CH_2)_3-$, $-CH_2CH(CH_3)-$ or $-CH_2C(CH_3)_2-$;
$R^3$ is

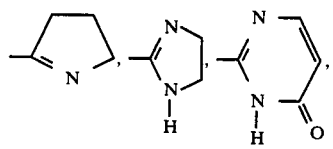

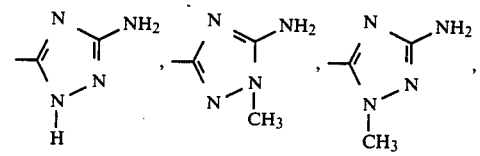

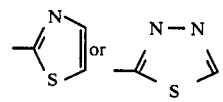

, and pharmaceutical compositions containing such compounds, have utility as anti-ischaemic and antihypertensive agents.

7 Claims, No Drawings

DIHYDROPYRIDINES AND THEIR USE IN TREATING CARDIAC CONDITIONS AND HYPERTENSION

This application is a continuation-in-part of Ser. No. 463,096, filed Feb. 2, 1983 now abandoned.

BACKGROUND OF THE INVENTION

This invention relates to certain dihydropyridines, specifically to certain 1,4-dihydropyridines having a heterocyclic-substituted piperazinyl group in the side chain attached to the 2-position, which have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the invention, there are provided novel 1,4-dihydropyridine derivatives of the formula:

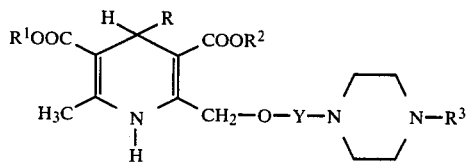

and their pharmaceutically acceptable acid addition salts;
where:
R is aryl or heteroaryl;
$R^1$ and $R^2$ are each independently $C_1$-$C_4$ alkyl or 2-methyoxyethyl;
Y is —$(CH_2)_2$—, —$(CH_2)_3$—, —$CH_2CH(CH_3)$— or —$CH_2C(CH_3)_2$—;
$R^3$ is

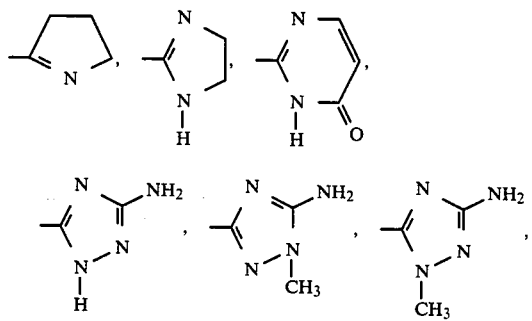

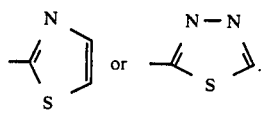

The term "aryl" as used in this specification, includes phenyl and phenyl substituted by, for example, one or two substituents selected from nitro, halo, $C_1$-$C_4$ alkyl, $C_1$-$C_4$ alkoxy, hydroxy, trifluoromethyl, ($C_4$-$C_4$ alkoxy)carbonyl and cyano. It also includes 1- and 2-naphthyl. "Halo" means F, Cl, Br or I.

The term "heteroaryl" as used in this specification for R means an aromatic heterocyclic group which may optionally be substituted and includes, for example, benzofuranyl; benzothienyl; pyridyl optionally monosubstituted by methyl or cyano; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$-$C_4$ alkyl.

Alkyl groups having 3 or more carbon atoms can be straight or branched chain.

R is preferably aryl substituted by 1 or 2 halo atoms or a single $CF_3$ group. The more preferred aryl groups represented by R are 2-chlorophenyl, 2-trifluoromethylphenyl, 2,3-dichlorophenyl, 3,5-dichlorophenyl, 2,6-dichlorophenyl, 1-naphthyl, 3-chlorophenyl and 2-fluorophenyl.

$R^1$ is preferably $CH_3$, $R^2$ is preferably $C_2H_5$, and Y is preferably —$(CH_2)_2$—.

Also included in the present invention are pharmaceutical compositions containing compounds of the present invention and a pharmaceutically acceptable diluent or carrier. The compounds of this invention can be administered to man in a method of preventing or treating cardiac conditions or a method of preventing or treating hypertension.

DETAILED DESCRIPTION OF THE INVENTION

The compounds of the formula (I) containing one or more asymmetric centres will exist as one or more pairs of enantiomers, and such pairs or individual isomers may be separable by physical methods, e.g. by fractional crystallization of the free bases or suitable salts or chromatography of the free bases. The invention includes the separated pairs as well as mixtures thereof, as racemic mixtures or as separated d- and l- optically-active isomeric forms.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

The compounds of the formula (I) can be prepared via a number of routes, including the following:

(1) Compounds in which $R^3$ is

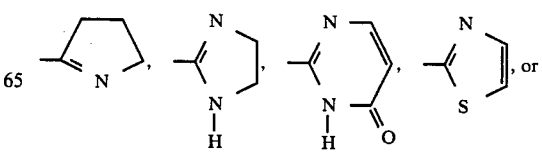

can be prepared as follows:

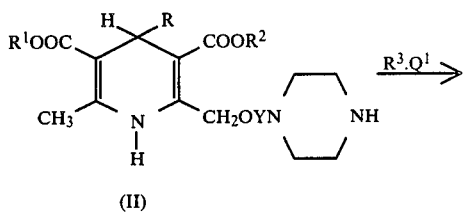

(II)

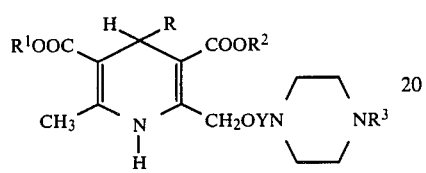

where $Q^1$ is a facile leaving group such as $C_1$-$C_4$alkoxy, (preferably methoxy or ethoxy), $C_1$-$C_4$ alkylthio (preferably methylthio), Cl or Br. The reaction is typically carried out by heating compound (II), optionally in acid addition salt form, and preferably under reflux, with the compound $R^3.Q^1$, and in a suitable organic solvent, e.g. ethanol. Generally reaction times of up to 24 hours are necessary. When $Q^1$ is Cl or Br, the presence of an acid acceptor such as triethylamine is desirable. The product can be isolated and purified conventionally.

The starting materials of the formula (II) are described and claimed in our U.K. application no. 8225246 filed on September 4, 1982 which corresponds to our U.S. patent application entitled "Dihydropyridine Derivatives" which was filed in the U.S. concurrently with this application; and are prepared by the removal of a suitable protecting group from the corresponding N-protected piperazine derivative, i.e.:

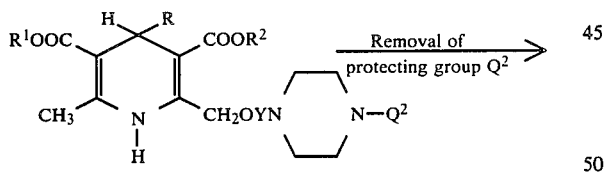

(II)

Preferred protecting groups are benzyl, 4-chlorobenzyl (both removable by hydrogenation) and trityl (removable by acid).

The N-protected piperazines are obtainable conventionally. The N-benzyl and N-(4-chlorobenzyl) derivatives are for example described and claimed in our European patent application publication no. 0060674 which is incorporated herein by reference.

Routes to these starting materials are as follows:

(a) Hantzsch synthesis:

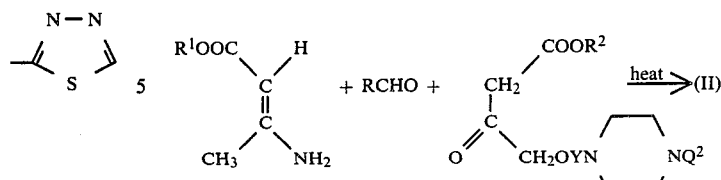

Either the ketoester and aldehyde are heated together first and then the crotonate is added, or all three reactants are heated together, as will be known to those skilled in the art, or (b)

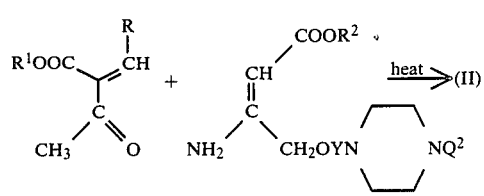

Generally the crotonate is prepared in situ by reaction of the corresponding acetoacetate:

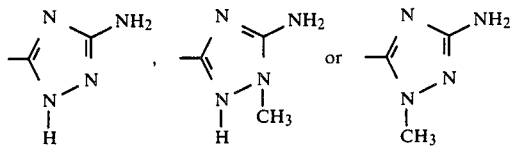

with ammonium acetate as is known to those skilled in the art.

(2) Compounds in which $R^3$ is

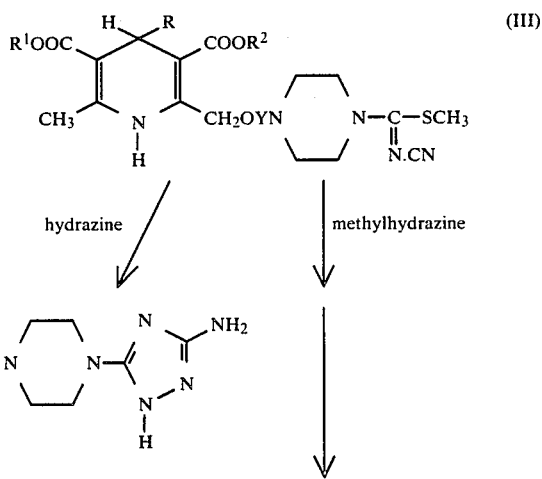

can be prepared as follows:

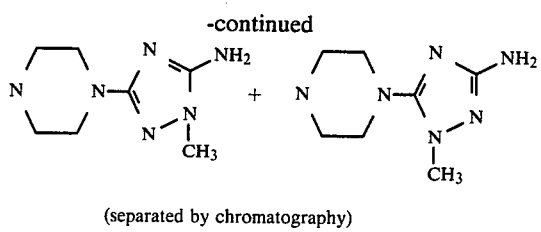

(separated by chromatography)

The reaction is typically carried out by heating the reactants together, preferably under reflux, in a suitable organic solvent, e.g. ethanol, for a few hours. When methylhydrazine is used, a mixture of the two N-methyl products is obtained, which can be separated by chromatography as described in Example 6.

The starting materials of the formula (III) are described and claimed in our copending U.K. application no. 8225246 filed on September 4, 1982. They are prepared as follows:

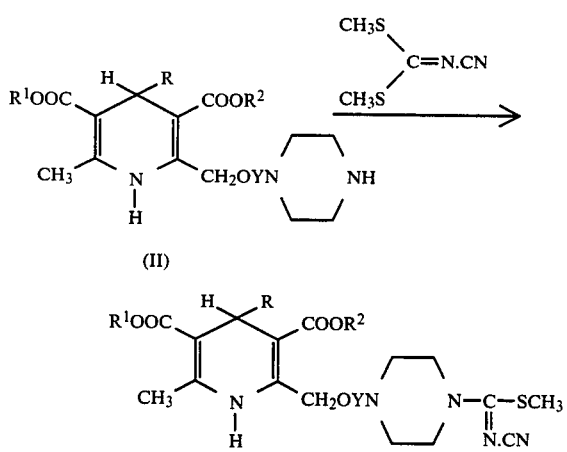

The reaction is typically carried out by stirring the reactants together at room temperature in a suitable organic solvent, e.g. isopropanol, for up to about 24 hours.

Acid addition salts can be prepared conventionally, e.g. by reacting a solution of the free base in a suitable organic solvent with a solution of the desired acid in a suitable solvent, and either recovering the salt by filtration where it precipitates from solution, or by evaporation of solution to dryness.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force tranducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds are generally in the range of from 2–100 mg daily for an average adult patient (70 kg). Thus for a typical adult patient, individual tablets or capsules generally contain from 1 to 10 mg of active compound, in a suitable pharmaceutically acceptable vehicle or carrier. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosages ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable acid addition salt thereof, together with a pharmaceutically acceptable diluent or carrier.

The invention also provides a method of protecting the heart from the deleterious effects of ischaemia, which comprises administering an effective amount of a compound of the formula (I) or pharmaceutically acceptable acid addition salt thereof, or pharmaceutical composition as defined above.

The invention also includes a method of treating hypertension which comprises administering an antihypertensive amount of a compound of the formula (I) or pharmaceutically acceptable acid addition salt thereof, or pharmaceutical composition as defined above.

The following Examples illustrate the invention. All temperatures are in °C.:

EXAMPLE 1

2-[2-(4-(1-Pyrrolin-2-yl)-piperazin-1-yl)ethoxymethyl]-4-(2-chlorophenyl)-3-ethoxycarbonyl-5-methoxycarbonyl-6-methyl-1,4-dihydropyridine

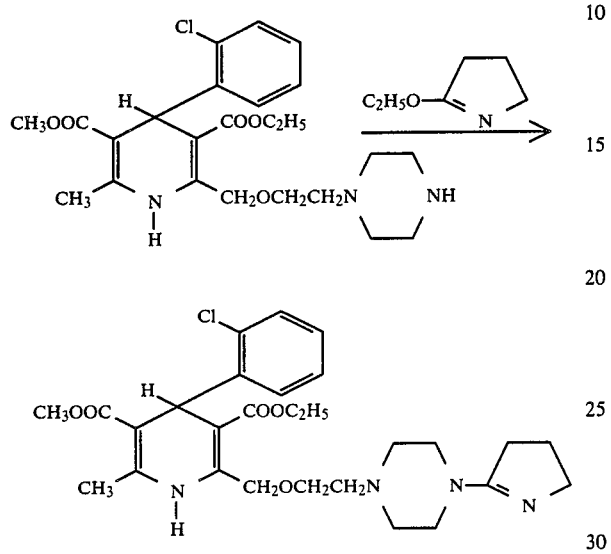

4-(2-Chlorophenyl)-3-(ethoxycarbonyl)-3-(methoxycarbonyl)-6-methyl-2-[2-(piperazin-1-yl)ethoxymethyl]-1,4-dihydropyridine (0.7 g) was dissolved in 10 ml of ethanol and converted to the oxalate salt by addition of a solution of 0.15 g of oxalic acid in 5 ml of ethanol. To this suspension was added 0.12 g of 2-ethoxypyrroline and the mixture was refluxed for 18 hours. The reaction mixture was then filtered through "Solka-floc" (Trade Mark) and evaporated to dryness. The resultant solid was basified with aqueous sodium carbonate solution and extracted with methylene chloride to give a white solid. After two crystallizations from diisopropylether, there was obtained 0.1 g of the title compound, m.p. 104°.

Analysis %: Found: C,61.70; H,6.89; N,10.28, Required for $C_{28}H_{37}ClN_4O_5$: C,60.92; H,6.84; N,9.93.

EXAMPLES 2 TO 4

The following compounds were prepared similarly to the previous Example, starting from the same piperazine (but without converting it to the oxalate salt) and the stated heterocycle $R^3.Q^1$, the products of Examples 2 and 3 being obtained in oxalate and dihydrochloride salt form, respectively, by treatment of the free base product with, respectively, oxalic acid in ether and hydrogen chloride in ether:

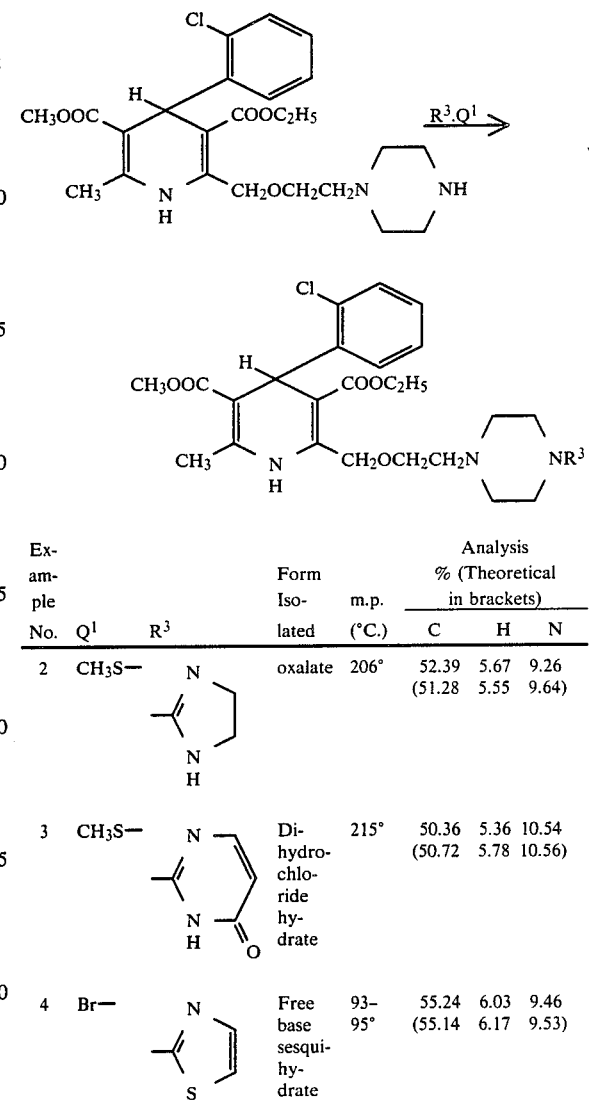

| Example No. | $Q^1$ | $R^3$ | Form Isolated | m.p. (°C.) | Analysis % (Theoretical in brackets) C | H | N |
|---|---|---|---|---|---|---|---|
| 2 | $CH_3S-$ | (1-pyrrolin-2-yl, N–H) | oxalate | 206° | 52.39 (51.28 | 5.67 5.55 | 9.26 9.64) |
| 3 | $CH_3S-$ | (pyrimidinon-2-yl, N–H, =O) | Dihydrochloride hydrate | 215° | 50.36 (50.72 | 5.36 5.78 | 10.54 10.56) |
| 4 | $Br-$ | (thiazol-2-yl) | Free base sesquihydrate | 93–95° | 55.24 (55.14 | 6.03 6.17 | 9.46 9.53) |

EXAMPLE 5

2-{2-[4-(5-Amino-1,2,4-triazol-3-yl)piperazine-1-yl]ethoxymethyl}-4-(2-chlorophenyl)-3-ethoxycarbonyl-5-methoxycarbonyl-6-methyl-1,4-dihydropyridine, bis-maleate hemihydrate (IIIA)

-continued

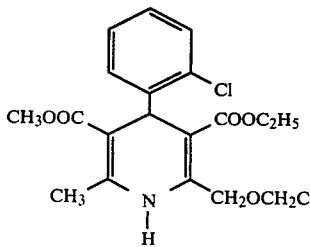

A mixture of 1.0 g of compound "IIIA" and 0.3 g of hydrazine hydrate in 5 ml or ethanol were refluxed on a steambath for 2 hours and then evaporated to dryness. The resultant oil was chromatographed on "Kieselgel 60" (Trade Mark) (5 g) and eluted with a mixture of 1% methanol in ethyl acetate to give 1.0 g of a pale yellow oil. This oil was dissolved in ethyl acetate and the maleate salt was prepared by addition of a solution of maleic acid in ether. The yellow precipitate so obtained was ground with fresh dry ether and crystallized from acetone to give 0.3 g of the title compound, m.p. 135° (d).

Analysis %: Found: C,50.83; H,5.56; N,12.20 Required for $C_{26}H_{34}ClN_7O_5 \cdot 2C_4H_4O_4 \cdot \frac{1}{2}H_2O$: C,50.97; H,5.91; N,12.24.

EXAMPLE 6

Preparation of:

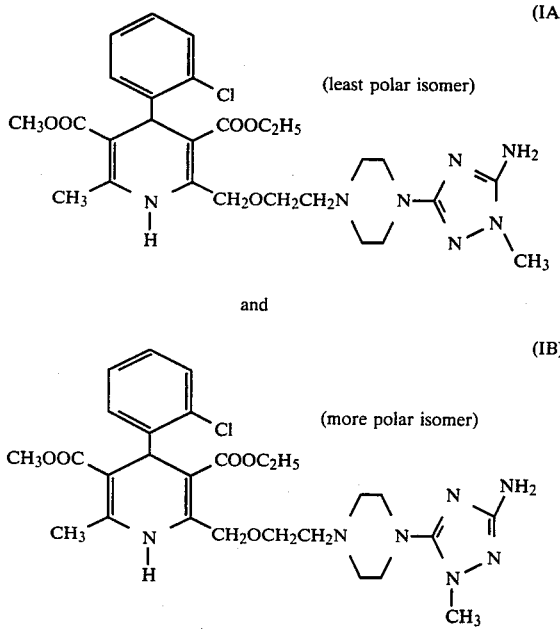

(IA) (least polar isomer)

and (IB) (more polar isomer)

Following a similar procedure to the previous Example, using the same piperazine and 0.3 g of methylhydrazine, a mixture of the two isomers (IA) and (IB) was obtained. These were separated by chromatography on 3 g of "Kieselgel 60" (Trade Mark) commencing with toluene and increasing the polarity of the eluent through methylene chloride to a 1% solution of methanol in methylene chloride. The least polar isomer, which was eluted first, was an oil which crystallised from diethyl ether to give 121 mg of 2-[2-(4-{5-amino-1-methyl-1,2,4-triazol-3-yl}-piperazin-1-yl) ethoxymethyl]-4-(2-chlorophenyl)-3-ethoxycarbonyl-5-methoxycarbonyl-6-methyl-1,4-dihydropyridine, m.p. 92°–96°.

Analysis %: Found: C,56.17; H,6.71; N,16.72 Required for $C_{27}H_{36}ClN_7O_5$: C,56.49; H,6.32; N,17.08.

The more polar isomer (which was eluted after the least polar isomer) crystallized from diethyl ether to give 36 mg of 2-[2-(4-{3-amino-1-methyl-1,2,4-triazol-5-yl}-piperazin-1-yl)ethoxymethyl]- 4-(2-chlorophenyl)-3-ethoxycarbonyl-5-methoxycarbonyl-6-methyl- 1,4-dihydropyridine hemihydrate, m.p. 93°–94°.

Analysis %: Found: C,55.62; H,6.24; N,16.45 Required for $C_{27}H_{36}ClN_7O_5 \cdot \frac{1}{2}H_2O$: C,55.61; H,6.40; N, 16.82.

The following Preparations illustrate the preparation of certain starting materials. All temperatures are in °C.

PREPARATION 1

4-(2-Chlorophenyl)-2-{2-[4-(2-cyano-1-methylthio-formimidoyl) piperazin-1-yl]ethoxymethyl}-3-ethoxycarbonyl-5-methoxycarbonyl-6-methyl-1,4-dihydropyridine, hydrochloride

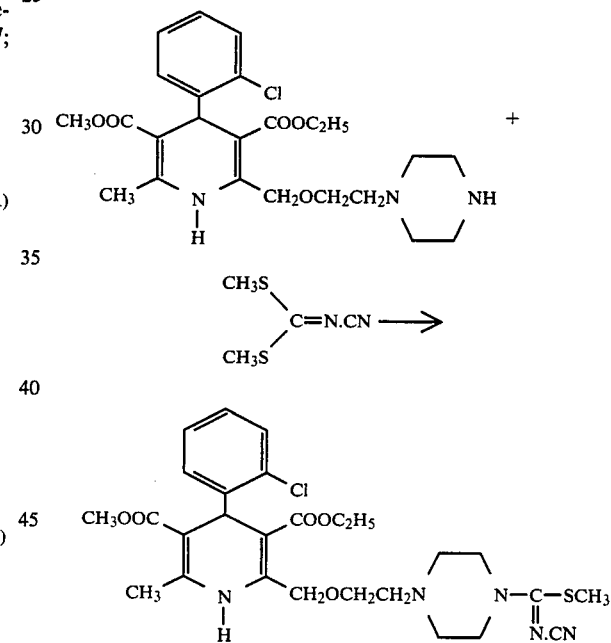

A mixture of 4-(2-chlorophenyl)-3-(ethoxycarbonyl)-5-(methoxycarbonyl)-6-methyl-2-[2-(piperazin-1-yl) ethoxymethyl]-1,4-dihydropyridine (2.8 g) and dimethyl N-cyanoimidodithiocarbonate (0.8 g) in 100 ml of isopropanol were stirred together at room temperature for 18 hours. The solvent was evaporated and the residual oil was chromatographed on 5 g of "Florisil" (Trade Mark) using toluene to give 1.5 g of an oil, part of which was used without further purification. 0.75 g of the free base product so obained was converted to its hydrochloride salt by the addition of ethereal hydrogen chloride to a solution of the free base in ethyl acetate. The resultant gum was triturated with either to give 328 mg of the title compound, m.p. 168°.

Analysis %: Found: C,52.92; H,5.84; N,11.71 Required for $C_{27}H_{34}ClN_5O_5S \cdot HCl$: C,52.94; H,5.76; N,11.43.

PREPARATION 2

Preparation of 4-(2-chlorophenyl)-3-ethoxycarbonyl-5-methoxycarbonyl-6-methyl-2-[2-(piperazin-1-yl)ethoxymethyl]-1,4-dihydropyridine, and its bis-oxalate salt.

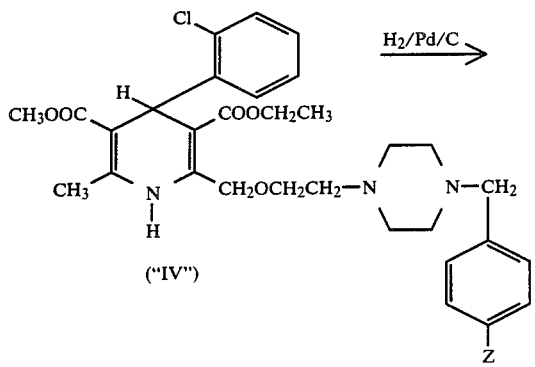

("IV")

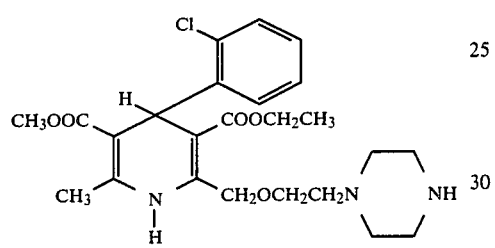

Method A: The bis-oxalate salt of the 4-chlorobenzyl-protected piperazine (IV, Z=Cl) (5 g) in methanol (1500 ml) was stirred and hydrogenated on a 5% palladium on charcoal catalyst (0.5 g) at 50 p.s.i. and room temperature overnight. The catalyst was filtered, the solvent removed by evaporation, and the residue partitioned between methylene chloride (100 ml) and dilute aqueous ammonia (100 ml). The organic phase was dried (Na$_2$CO$_3$) filtered and evaporated to dryness to give the title compound as the free base, an oil (3 g). A sample converted to the bis-oxalate salt in acetone had a m.p. 170° (decomposes).

Analysis %: Found: C,51,72; H,5.58; N,6.54 Required for C$_{24}$H$_{32}$ClN$_3$O$_5$.2(C$_2$H$_2$O$_4$): C,51.03; H,5.66; N,6.38.

Method B: The benzyl-protected piperazine (IV, Z=H) (42 g) in methanol (1500 ml) and acetic acid (9 ml) was hydrogenated at 40° under 50 p.s.i. on a 5% palladium on charcoal catalyst (2 g) overnight. Treatment as in Method "A" gave the title compound as the bis-oxalate salt (19 g), identical to the salt obtained by Method "A".

The starting 4-chlorobenzyl- and benzyl-piperazines are described in Examples 34 and 38 respectively of our copending European Patent Application Publication No. 0060674, which is incorporated herein by reference. The route used to them was as follows:

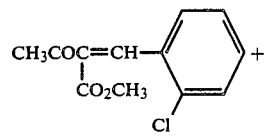

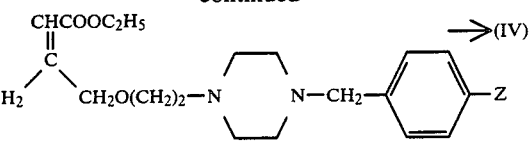

Activity Data

The molar concentration of the compounds required to reduce the response by 50% in the test specified on pages 9–10 is given below (IC$_{50}$ values) (1M=1 gm. mole/liter). The smaller the concentration, the more active the compound.

| Compound | IC$_{50}$ Values IC$_{50}$ |
|---|---|
| Product of Example 1 | 1.41 × 10$^{-7}$ M |
| Product of Example 2 | 1.0 × 10$^{-7}$ M |
| Product of Example 3 | 3.6 × 10$^{-8}$ M |
| Product of Example 4 | 1.5 × 10$^{-8}$ M |
| Product of Example 5 | 3.8 × 10$^{-8}$ M |
| Product of Example 6 (least polar isomer) | 2.6 × 10$^{-8}$ M |
| Product of Example 6 (more polar isomer) | 1.0 × 10$^{-7}$ M |

We claim:

1. A 1,4-dihydropyridine derivative of the formula:

$$R^1OOC \underset{H_3C}{\overset{H,R}{\diagdown}} COOR^2$$
$$\text{(dihydropyridine with } CH_2-O-Y-N\diagup\diagdown N-R^3\text{)}$$

or a pharmaceutically acceptable acid addition salt thereof, wherein:

R is aryl or heteroary;
R$^1$ and R$^2$ are each independently C$_1$-C$_4$ alkyl or 2-methoxyethyl;
Y is —(CH$_2$)$_2$—, —(CH$_2$)$_3$—, —CH$_2$CH(CH$_3$)— or —CH$_2$C(CH$_3$)$_2$—; and
R$^3$ is (structures shown)

wherein said aryl group is phenyl; phenyl substituted by one or two substituents selected from the group consisting of nitro, halo, C$_1$-C$_4$ alkyl, C$_1$-C$_4$ alkoxy, hydroxy, trifluoromethyl, (C₁–C₄ alkoxy)-carbonyl and cyano; 1-naphthyl; or 2-naphthyl; and wherein said heteroaryl group is benzofuranyl; benzothienyl; pyridyl; pyridyl substituted by methyl or cyano; quinolyl; benzoxazoyl; benzthiazolyl; furyl; pyrimidinyl; thiazolyl; 2,1,3-benzoxadiazol-4-yl; 2,1,3-benzthiadiazol-4-yl; thienyl; or thienyl substituted by halo or C₁–C₄ alkyl.

2. A compound according to claim 1 wherein R is aryl.

3. A compound according to claim 1 wherein R is heteroaryl.

4. A compound according to claim 1 wherein R is 2-chlorophenyl, R¹ is CH₃, R² is C₂H₅, Y is —(CH₂)₂— and R³ is:

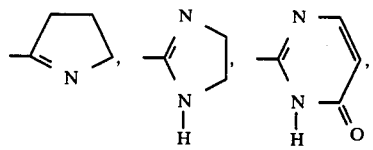

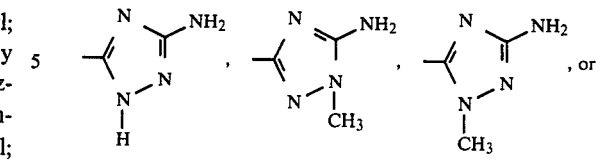

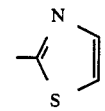

5. A pharmaceutical composition comprising a cardiac condition treating or antihypertensive effective amount of a compound according to claim 1 and a pharmaceutically acceptable diluent or carrier.

6. A method of treating cardiac conditions which comprises administering a cardiac condition treating effective amount of a compound according to claim 1.

7. A method of treating hypertension which comprises administering an anti-hypertensive effective amount of a compound according to claim 1.

* * * * *